US00PP18127P2

(12) United States Plant Patent
Egger

(10) Patent No.: US PP18,127 P2
(45) Date of Patent: Oct. 16, 2007

(54) ***HEUCHERA* PLANT NAMED 'RAVE ON'**

(50) Latin Name: ***Heuchera* hybrid**
Varietal Denomination: Rave On

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 36 days.

(21) Appl. No.: 11/388,936

(22) Filed: Mar. 24, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—June Hwu
(74) *Attorney, Agent, or Firm*—Klarquist Sparkman, LLP

(57) ABSTRACT

A new and distinct hybrid of *Heuchera* plant characterized by masses of wand type flowering stems in the spring, numerous rose pink flowers, small, silver veiled, dark to greenish leaves, a mounding habit, and good vigor.

1 Drawing Sheet

Botanical denomination: *Heuchera* hybrid.
Variety designation: 'Rave On'.

The present invention relates to a new and distinct cultivar of *Heuchera* hybrid and given the cultivar name of 'Rave On'. *Heuchera* is in the family Saxifragaceae. *Heuchera* 'Rave On' originated from a planned cross between two unknown, unpatented, proprietary *Heuchera* plants. Given its ornamental foliage and flower form, it is probable that *Heuchera sanguinea, H. micrantha, H. americana,* and *H. cylindrica* are in its parentage.

This new *Heuchera* is distinguished by:

1. Masses of wand type flower stems in the spring.
2. Numerous rose pink flowers on each flower stem.
3. Small, silver veiled, dark to greenish leaves.
4. Mounding habit.
5. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg. shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

The drawing shows a one-year-old plant of *Heuchera* 'Rave On' growing in the ground in full sun in the trial fields in May in Canby, Oreg.

DETAILED PLANT DESCRIPTION

The following is a detailed description of the new *Heuchera* cultivar based on observations taken in May of a two-year-old specimen grown a 5 gallon container in an open air shade house with 50% shade cover and added irrigation in the summer months in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Form.*—Basal rosette, herbaceous perennial.
*Hardiness.*—USDA Zone 4 to 9.
*Size.*—17 cm tall from the ground to the top of the foliage and 40 cm wide.
*Habit.*—Mounding.
*Vigor.*—Excellent.
*Roots.*—Fibrous, freely branching, fine, and white in color. Roots develop easily from cuttings.

Leaf:

*Type.*—Simple.
*Arrangement.*—Rosette.
*Shape.*—Broadly ovate.
*Lobing/division.*—7 scalloped lobes, overlapping, each notched 1 to 4 times.
*Venation.*—Palmate.
*Margins.*—Broadly crenate, slightly undulate, glandular.
*Apex.*—Mucronulate.
*Base.*—Cordate, lobes overlapping at the base, with one lobe spiraling in.
*Blade size.*—5 to 7 cm long and 4.5 to 6.7 cm wide.
*Surface texture.*—Glandular hairs on top and bottom surfaces.
*Petiole description.*—13 to 14 cm long and 2 mm wide with the surface having very short glandular hairs, color is Greyed Green 197A to Yellow Green 147A.
*Leaf color.*—Abaxial — Greyed Green 198B overall but margins and veins which are closest to Yellow Green 147A but browner, lightening to Yellow Green 147A by summer. Adaxial — Between Brown 200C and Greyed Purple 187B.

Inflorescence:

*Type.*—Thyrse, in a tight wand shape. A wand type flower is where the flowers a held tightly next to the peduncle and near the end of the peduncle.
*Number of flowers.*—About 140 per thyrse.
*Number of thyrse in spring.*—29 in the first flush.

*Peduncle.*—52 cm tall and 3 mm wide at the base, Brown 200A, glandular hairs, 3 to 5 cauline leaves, ovate to orbicular, grow to 5 cm long and 4.5 cm wide, colored, lobed and margined the same as the stem leaves.

*Pedicel.*—Variable in length, Greyed Purple 187A, with glandular hairs.

*Bloom period.*—May in Canby, Oreg.

Flower bud:

*Size.*—2.5 mm wide and 4.5 mm long.

*Description.*—Glandular, ovoid, down facing.

*Color.*—Red 53C.

Flower:

*Type.*—Perfect, zygomorphic.

*Shape.*—Campanulate.

*Size.*—6 mm long and 5 mm wide.

*Petal description.*—5, pink, Red Purple 63B on both sides, oblanceolate with a clawed base, tip acute, margin entire, glandular hairs on back side, reflexed slightly, 3 mm long and 0.8 mm wide.

*Calyx description.*—Campanulate, 5 lobes, divided ½ way to the base, glandular on back side, tips acute, margin entire, 6 mm long and 5 mm wide.

*Calyx and overall flower color.*—Inside: Red 55B. Outside: Red Purple 63B with lobe tips Red Purple 59A.

*Stamen description.*—5 in number, filaments 0.9 mm long, White 155D, anthers sterile, no pollen produced, oval, 1 mm long, Red 53D.

*Pistil description.*—5 mm long, stigma and style are White 155A, stigma is 2 parted, and ovary is Yellow Green 150A.

*Fragrance.*—None.

*Lastingness.*—Each thyrse blooms for about 3 weeks on the plant.

Fruit:

*Type.*—Two-beaked ovoid capsule.

*Color.*—Brown 200D.

Seed:

*Shape.*—Linear.

*Size.*—2 mm long.

*Color.*—Black 202A.

Pest and disease tolerance: Excellent disease resistance to powdery mildew, the common problem of *Heuchera*. No known resistance to *Heuchera* rust and root weevils.

COMPARISON TO SIMILAR *HEUCHERA*

Compared to *Heuchera* 'Hollywood' (U.S. Plant Pat. No. 17,129) this new variety has a smaller greener leaves, a heavier silver veil, taller flowering stems, and rose pink rather than coral colored flowers.

I claim:

1. A new and distinct hybrid of *Heuchera* plant as herein illustrated and described.

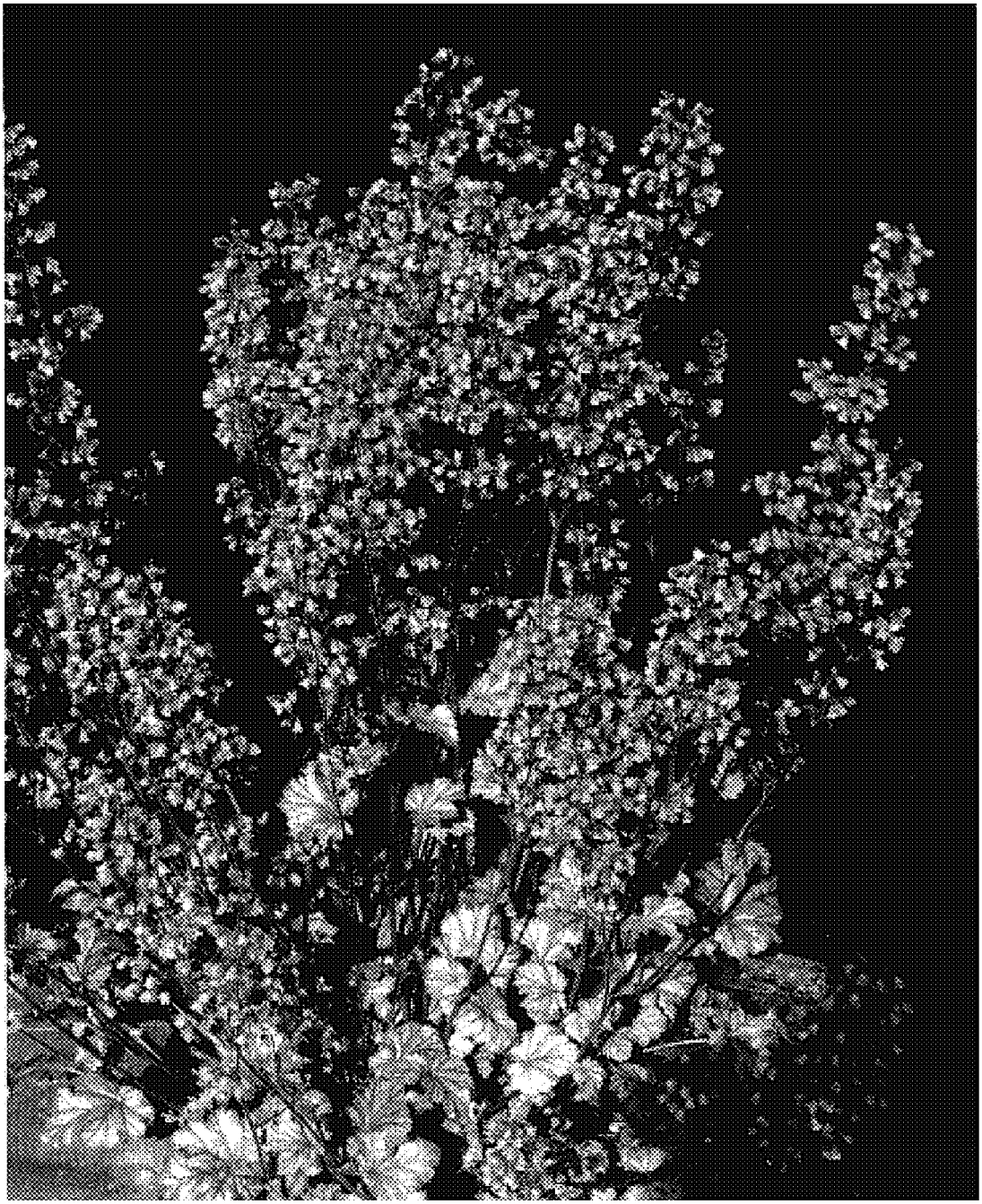

* * * * *